United States Patent
Smith et al.

(10) Patent No.: US 7,570,152 B2
(45) Date of Patent: Aug. 4, 2009

(54) METHOD AND APPARATUS FOR TEMPORARILY DISABLING A PATIENT MONITOR

(75) Inventors: Toby E. Smith, Broken Arrow, OK (US); Craig L. Cooper, Inola, OK (US)

(73) Assignee: Bed-Check Corporation, Tulsa, OK (US)

( * ) Notice: Subject to any disclaimer, the term of this patent is extended or adjusted under 35 U.S.C. 154(b) by 345 days.

(21) Appl. No.: 11/507,418

(22) Filed: Aug. 21, 2006

(65) Prior Publication Data

US 2007/0040692 A1 Feb. 22, 2007

Related U.S. Application Data

(60) Provisional application No. 60/709,616, filed on Aug. 19, 2005.

(51) Int. Cl.
G08B 5/22 (2006.01)
(52) U.S. Cl. .................. 340/286.07; 340/539.12; 340/573.1
(58) Field of Classification Search ................ 340/539.12–539.15, 573.1–573.4, 286.07
See application file for complete search history.

(56) References Cited

U.S. PATENT DOCUMENTS

| | | | |
|---|---|---|---|
| 3,986,161 A | 10/1976 | MacKellar | |
| 4,484,043 A | 11/1984 | Musick et al. | |
| 4,565,910 A | 1/1986 | Musick et al. | |
| 4,633,237 A | 12/1986 | Tucknott et al. | |
| 4,907,845 A | 3/1990 | Wood | |
| D361,462 S | 8/1995 | Newham | |
| 5,554,835 A | 9/1996 | Newham | |
| 5,600,108 A | 2/1997 | Newham | |
| 5,623,760 A | 4/1997 | Newham | |
| 5,633,627 A | 5/1997 | Newham | |
| 5,640,145 A | 6/1997 | Newham | |
| 5,654,694 A | 8/1997 | Newham | |
| 5,780,798 A | 7/1998 | Hall-Jackson | |
| 5,796,059 A | 8/1998 | Boon | |
| 5,844,488 A | 12/1998 | Musick | |
| 5,945,914 A | 8/1999 | Holmes et al. | |
| 6,065,727 A | 5/2000 | Fitzgerald et al. | |
| 6,078,261 A | 6/2000 | Davsko | |
| 6,111,509 A | 8/2000 | Holmes | |

(Continued)

FOREIGN PATENT DOCUMENTS

EP 1 623 666 A2 2/2006

OTHER PUBLICATIONS

Smart Caregiver Corp. advertisement for Fall Monitors, Jun. 2005, Published in: US.

(Continued)

*Primary Examiner*—Brent Swarthout
(74) *Attorney, Agent, or Firm*—Fellers, Snider, Blankenship, Bailey & Tippens, P.C.; Terry L. Watt

(57) ABSTRACT

In accordance with a first preferred aspect of the instant invention, there is provided a patient monitor that is automatically disabled when a caregiver enters a room and then is automatically reactivated after the caregiver leaves. According to a first preferred embodiment, it will remain disabled during the time the caregiver is proximate to the patient/monitor and then will automatically reactivate after the caregiver has moved away.

6 Claims, 2 Drawing Sheets

U.S. PATENT DOCUMENTS

| | | |
|---|---|---|
| 6,292,102 B1 | 9/2001 | Smith |
| 6,307,476 B1 | 10/2001 | Smith et al. |
| 6,417,777 B2 | 7/2002 | Fitzgerald et al. |
| 6,441,742 B1 | 8/2002 | Lovely et al. |
| 6,544,200 B1 | 4/2003 | Smith et al. |
| 6,646,556 B1 | 11/2003 | Smith et al. |
| 6,696,653 B1 | 2/2004 | Fitzgerald et al. |
| 6,784,787 B1 | 8/2004 | Atkins et al. |
| 6,847,301 B1 | 1/2005 | Olson |
| 6,858,811 B2 | 2/2005 | Fitzgerald et al. |
| 6,864,795 B2 | 3/2005 | Smith et al. |
| 6,876,303 B2 * | 4/2005 | Reeder et al. ............ 340/573.1 |
| 6,897,781 B2 | 5/2005 | Cooper et al. |
| 6,987,232 B2 | 1/2006 | Smith et al. |
| 6,998,986 B2 * | 2/2006 | Smith ...................... 340/573.1 |
| 7,030,764 B2 | 4/2006 | Smith et al. |
| 7,079,036 B2 | 7/2006 | Cooper et al. |
| 2002/0103674 A1 * | 8/2002 | Reeder et al. .................. 705/3 |
| 2003/0055685 A1 * | 3/2003 | Cobb et al. .................... 705/3 |
| 2004/0034389 A1 | 2/2004 | Chen et al. |
| 2004/0201487 A1 | 10/2004 | Benson et al. |
| 2005/0168341 A1 * | 8/2005 | Reeder et al. ............ 340/573.1 |
| 2006/0049936 A1 | 3/2006 | Collins et al. |

OTHER PUBLICATIONS

Smart Caregiver Corp. Advertisement for New Fall Monitor & Caregiver Key, Apr. 2005, Published in: US.

Smart Caregiver Corp. Advertisement for New Fall Monitors and Caregiver Key, May 2005, Published in: US.

Smart Caregiver Corp. Advertisement for Safety Monitor and Door Monitor, Mar. 2003, Published in: US.

Smart Caregiver Corp. Advertisement for Fall Guard and Attendant Monitors and Caregiver Key, Nov. 2004 , Published in: US.

Smart Caregiver Corp., page from catalog re Fall Guard Monitor, Oct. 2004, Published in: US.

Smart Caregiver Corp. Advertisement for Safety Monitor, , Published in: US.

* cited by examiner

METHOD AND APPARATUS FOR TEMPORARILY DISABLING A PATIENT MONITOR

FIELD OF THE INVENTION

This invention relates generally to patient monitoring systems and more particularly concerns devices and systems used to monitor seated, lying, or partially ambulatory patients in homes or in medical environments such as hospitals, institutions, and other care-giving environments wherein an alarm or other reminder is produced in response to a patient's condition.

BACKGROUND OF THE INVENTION

It is well known that the use of electronic devices to monitor a patient's status is a growing trend in healthcare settings. This trend can be attributed to any number of factors including the increased vigilance that can be obtained with electronic monitoring (e.g., electronic monitors never sleep or leave the patient's vicinity for a break), decreased staffing costs (e.g., one caregiver can cover multiple patients), etc.

As a specific example of a patient condition that is especially suitable for electronic monitoring, consider the use of electronic patient monitors to help reduce the risk of a patient fall. By way of general background, a fall places a patient at risk of various injuries including sprains, fractures, and broken bones—injuries which in some cases can be severe enough to eventually lead to a fatality. Of course, those most susceptible to falls (e.g., the elderly and post surgical patients) are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff training and identification and monitoring of high-risk hospital patients and nursing home residents.

Of course, direct monitoring high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a caregiver who might be located either nearby or remotely at a central monitoring facility, such as a nurses' station. The obvious advantage of an electronic monitoring arrangement is that it frees the caregiver to pursue other tasks away from the patient. Additionally, when the monitoring is done at a central facility a single nurse can monitor multiple patients which can result in decreased staffing requirements.

Generally speaking, electronic monitors work by first sensing an initial status of a patient, and then generating a signal when that status changes, e.g., he or she has sat up in bed, left the bed, risen from a chair, etc., any of which situations could pose a potential cause for concern in the case of an at-risk patient. Electronic bed and chair exit monitors typically use a pressure sensitive switch in combination with a separate monitor/microprocessor. In a common exit monitor arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is sensed by the microprocessor. The software logic that drives the monitor is typically programmed to respond to the now-opened circuit by triggering some sort of alarm—either electronically (e.g., to the nursing station via a conventional nurse call system) or audibly (via a built-in audio alarm).

However, the increasing use of electronic patient monitors is not without its problems. For example, and focusing for the moment on patient exit monitors, the use of such monitors can pose a problem for the staff who might have the responsibility of turning the patient at prescribed intervals, bathing the patient, etc. More particularly, when the caregiver needs to work with the patient a necessary first step is to disable the exit monitor, typically by pressing a "reset" or "hold" button or similar switch provided for that purpose on the exterior of the monitor. However, even the most attentive staff can all too easily forget to reactivate the monitor before exiting, thereby leaving the patient at risk for a fall thereafter. Further, direct contact with a patient monitor—even a contact as fleeting as pressing a "hold" or "reset" switch—can potentially act as a conduit for the spread of bacteria and germs. Of course, these concerns become even more pressing if the patient is in isolation.

More generally, in view of the ever-increasing reliance on electronic patient monitoring of all sorts, a caregiver may be confronted with a wide variety of audio alarms when he or she enters a room. In addition to the bed exit monitors described previously, ventilators, cardiac monitors, IV fluid dispensers, vacuum collection systems, medication pumps, wetness monitors, pressure sore monitors, etc., may each have its own audio alarm. Of course, the purpose of these alarms is to alert the caregiver to potential problems and draw the caregiver into the room. However, once the caregiver has arrived, such alarms have served their purpose and rapidly become a detriment to patient care. For example, the sounds of such alarms may make communication with the patient or another caregiver difficult and may frighten or unnecessarily disturb the patient. As a consequence, the caregiver's first act upon entering the room is usually to silence the alarm(s), rather than to first attend to the emergency that triggered the alarm.

Others have considered this or related problems but the solutions heretofore proposed have generally not been without problems. For example, it is known to provide an electronic patient monitor that can accept a key therein, the purpose of the key being to block access by an enterprising patient to the reset (or, more generally, deactivation) switch. So long as the key is absent, the monitor cannot be reset or otherwise disabled. So, when the caregiver enters the room in response to an alarm, insertion of the key into a receptacle on the monitor's body is a necessary prerequisite to silencing the alarm. However, this sort of configuration can only delay the response of the caregiver to the patient even further, as two operations must now be performed to silence the alarm (insert the key and then press the reset switch) as compared with the single operation that was required previously.

Additionally, sensors other than mat-type pressure sensing switches may be used in patient monitoring including, without limitation, temperature sensors (e.g., U.S. patent Ser. No. 11/132,772), patient activity sensors, toilet seat sensors (see, e.g., U.S. Pat. No. 5,945,914), wetness sensors (e.g., U.S. Pat. No. 6,292,102), pressure sore sensors (e.g., U.S. Pat. No. 6,646,556), etc., all of which are incorporated herein by reference. Thus, in the text that follows the terms "mat" or "patient sensor" should be interpreted in its broadest sense to apply to any sort of patient monitoring switch or device, whether the sensor is pressure sensitive or not.

Finally, technology concerned with reducing the need for caregiver intervention may be found in issued U.S. Pat. No. 6,897,781, also incorporated herein by reference, discusses how white noise can be used in the context of pressure sore prevention.

Heretofore, as is well known in the patient monitoring arts, there has been a need for an invention to address and solve the above-described problems. There has been for some time a need for a device that can assist the caregiver by automatically disabling a patient monitor while the caregiver is in the room and/or working with a patient and which will thereafter automatically reactivate the exit monitor after the caregiver has exited the vicinity of the patient. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first preferred aspect of the instant invention, there is provided a patient monitor that has an alarm function that is automatically disabled or suspended when a caregiver enters a room and then is automatically reactivated again after the caregiver leaves. According to a first preferred embodiment, the alarm component of the monitor will remain disabled or silenced during the time the caregiver is proximate to the patient/monitor and then will automatically reactivate after the caregiver has moved away.

In one variation, the caregiver will carry (preferably in the form of a badge, pager, PDA or cell phone, etc.) an electronic device that transmits an inhibiting signal to a receiver that is preferably located within each patient monitor in the room. In one preferred embodiment, the transmitter will generate an ultrasonic pulse train (e.g., a pulse might be generated every second or, in some embodiments at longer or shorter intervals as needed). According to the present embodiment, within each monitor will preferably be an ultrasonic receiver that, upon receipt, recognition, and verification (e.g., receipt of 3 or more consecutive pulses or some other recognizable code) of the appropriate signal, will suspend broadcast of its audio alarm and/or, suspend transmission of the alarm to a remote site such as a nurses' station (e.g., cancel the nurse call), and/or suspend the patient monitoring function of the unit. Note that visual alarm cues (such as flashing lights, warning messages on a computer monitor, etc.) might or might not be suspended according to the preferences of the programmer and the caregiver. The alarm functionality will remain suspended/disabled until such time as the caregiver leaves the proximity of the patient and the associated electronic monitors, at which time the functionality will preferably be fully and immediately restored so that if a problem remains uncorrected, an audible alarm can be sounded while the caregiver is still in the vicinity of the patient.

According to another preferred embodiment, there is provided a patient monitor substantially as described above that will be able to sense when a caregiver is proximate to the monitor/patient, will temporarily suspend the operation of one or more of its functions and, then will be automatically reactivated after the passage of a predetermined period of time.

According to still another preferred aspect of the invention, there is provided a patient monitor that can be manually disabled by sensing the transmission of an inhibiting signal while a caregiver is proximate to a patient and then that automatically reactivates/resumes monitoring and alarming after detecting that the caregiver has left the vicinity of the patient or at a point in time where an inhibiting signal is no longer detected (e.g., if the caregiver manually terminates the inhibiting broadcast, thereby reactivating the alarm functionality to determine whether the condition which caused the caregiver to be summoned to the room has been resolved).

In one preferred arrangement, the caregiver will carry, preferably in the form of a badge, a hand held device, etc., an electronic device that, upon activation, transmits an ultrasonic signal to a receiver that is preferably located within each electronic patient monitor in the room. In one preferred embodiment, the nurse or other caregiver will manually activate the transmitting device by pressing a switch that is integral thereto, thereby preferably initiating the transmission of an ultrasonic pulse train (e.g., a pulse will be transmitted every second or, in some embodiments, at longer or shorter time intervals as needed). Within each patient monitor will preferably be an ultrasonic receiver that, upon receipt, recognition, and verification (e.g., receipt of one or more consecutive pulses at the proper frequency and time spacing) of the appropriate signal, will preferably suspend broadcast of its audio alarm, suspend transmission of the alarm to a remote site such as a nurses' station, and/or suspend the monitoring function of the unit. Note that the monitor's visual alarm cues (such as flashing lights, etc.) might or might not be suspended according to the preferences of the programmer/or caregiver.

In another preferred embodiment, the monitor will continuously check for the presence of an ultrasonic pulse and, upon receipt of such pulse, will extend the alarm suspension by a period of time at least as long as the pulse interval (or, a time period sufficient to encompass two, three, etc., pulse intervals). Then, after some period of signal non-detection, the monitor will return to full functionality, preferably immediately after it is determined that the suppressing signal is absent.

In another preferred arrangement, the caregiver will be provided with a magnet that is preferably tethered to his or her clothing or to some item of equipment carried by the caregiver such as a key chain. In this variation, the magnet will preferably be placed on the face of the monitor, thereby indicating the presence of a health giver and signaling to the monitor that it is to cease its monitoring and/or its alarming activity. Within the monitor will preferably be a Reed, Hall effect, or similar proximity component that is capable of sensing when the magnet is in place. During the time that the magnet is in place, the patient monitor will preferably suspend its monitoring and/or alarming function. After the magnet is removed from its face, the monitor will preferably immediately resume its normal operations.

According to still another preferred embodiment, there is provided an apparatus for temporarily suspending the operation or alarm of a patient monitor which is substantially as described above, but wherein a plurality of signals are potentially receivable by the patient monitor. In this arrangement, different caregiver transmitters might generate different signals. In turn, the monitors would then be programmed to suspend their alarms (or not) upon receipt of different ones of the transmitted signals. For example, cardiac monitors might be programmed to suspend operation upon receipt of one signal and exit monitors upon receipt of a different signal. In this instance, transmitters that control the alarming of the critical cardiac monitor would only be given to nurses/caregivers with cardiac training. Thus, an orderly or nurse aid—who might be fully qualified to respond to an exit alarm, but unqualified to handle a cardiac emergency, would not automatically silence the cardiac monitor upon entry into the room. On the other hand, the nurse's transmitter would preferably silence both alarms.

In another preferred variation, the transmitted signal will reflect a hierarchy of responsibility and/or authority, with individuals who have higher levels of training and expertise (and perhaps a higher title) being given transmitters that broadcast a signal that is identifiable as belonging to such a person. Upon identification of a predetermined signal pattern, the monitor could be programmed to allow modification of its operating parameters by the user. That is, it may be that an orderly is fully qualified to respond to a bed exit alarm but should not be allowed to adjust monitor operating parameters such as exit delay, etc. On the other hand, a nurse would be qualified to make such an adjustment. By giving different transmitters to nurses and orderlies, the hospital or other institution can protect its patients against the possibility of inadvertent reprogramming of its devices. Obviously, in an extreme case, each individual in this care facility could be given a badge or other transmitter that emits a unique signal, thereby making it possible for the monitor to identify, and possibly record the identity of, the individual who is in the room.

In another preferred arrangement, there is provided an apparatus for temporarily suspending one or more functions or alarms of a patient monitor wherein a transmitted signal (or, alternatively, termination of an inhibiting signal) is utilized to automatically reactivate the alarms that were previously silenced while the caregiver is still in the room. This function could prove to be useful where a caregiver enters the room and automatically deactivates the various alarms, but thereafter determines that additional assistance may be needed from other of the staff. In such an instance, the transmitter will preferably be provided with a signal (or, alternatively, termination of an inhibiting signal) that notifies the monitor(s) to resume sounding of their alarms, irrespective of the fact that the caregiver is still present. Note that in this context the term "signal" is used in the broadest possible sense to include instances where the transmitter emits a distinctive canceling signal or combination or signals (e.g., one that is longer in duration, different in frequency or frequencies, etc., from the inhibiting signal or, alternatively, in its simplest form, deliberate cessation of the suppression/inhibiting signal) at the request of the caregiver. Alternatively, if the caregiver's transmitter ceases to broadcast its inhibiting signal, the monitor(s) in the room will preferably resume their normal operations upon a failure to detect the caregiver's signal.

In still another preferred arrangement, a patient's monitor(s) will be placed on hold or otherwise silenced when the door to the room is opened. Obviously, this approach would not be effective for some facilities, but in others where doors are kept closed most of the time (e.g., at assisted living centers, where the patients may be suffering from dementia, where the patients are criminals, etc.) this could be a preferred approach.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

In accordance with a preferred aspect of the instant invention, there is provided a patient monitor that will be disabled when a caregiver enters a room and that is automatically reactivated after the caregiver leaves. Preferably, at least the monitor's alarm function will remain disabled during the time the caregiver is proximate to the patient, with the alarm and other functions being automatically reactivated after the caregiver has moved away. In a preferred scenario, the instant monitor would be used in connection with a patient exit monitor, thereby allowing the caregiver to maneuver the patient within the bed or chair (or to temporarily remove the patient therefrom) without triggering the alarm.

GENERAL ENVIRONMENT OF THE INVENTION

Figure 1:
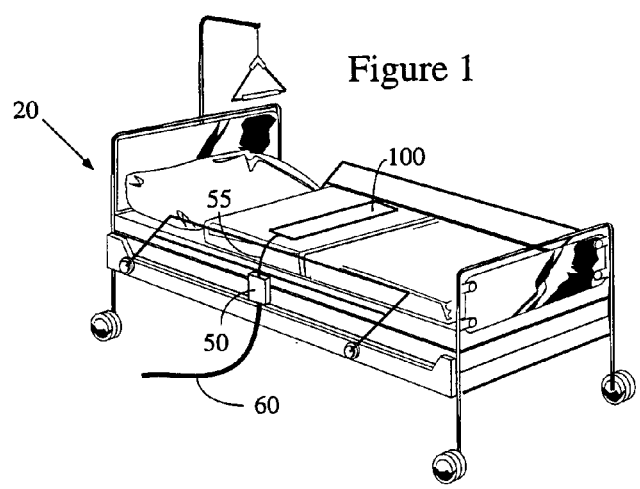
FIG. 1 illustrates the general environment of the instant invention, wherein an electronic monitor/mat combination is used to monitor a patient in a bed.

Turning first to FIG. 1 wherein the general environment of one specific embodiment of the instant invention is illustrated, in a typical arrangement a pressure sensitive mat 100 sensor is placed on a hospital bed 20 where it will lie beneath a weight-bearing portion of the reclining patient's body, usually the buttocks and/or shoulders. Generally speaking, the mat 100/electronic monitor 50 combination works as follows. When a patient is placed atop the mat 100, pressure generated by the patient's weight compresses it, thereby closing an internal electrical circuit. This circuit closure is sensed by the associated electronic patient monitor 50 and, depending on its design, this circuit closure may signal the monitor 50 to begin monitoring the patient via the sensing mat 100. Additionally, in some embodiments, the monitoring phase is initiated manually by the caregiver using a switch on the exterior of the monitor 50 that has been provided for that purpose.

After the monitoring function is engaged, if the patient attempts to leave the support surface, weight is removed from the sensing mat 100, thereby breaking its internal electrical circuit, which interruption is sensed by the attached electronic patient monitor 50. The patient monitor 50, which conventionally contains a microprocessor therein, then signals the caregiver per its pre-programmed instructions. In some cases, the signal will amount to an audible alarm or siren that is emitted from the unit 50. In other cases, an electronic signal could also be sent to a remote nurses/caregivers station wirelessly or via electronic communications line 60. In still another preferred arrangement, the patient monitor 50 will sound an audio alarm locally and simultaneously send the alarm signal to the nurses station. Note that additional electronic connections not pictured in this figure might include a monitor power cord to provide a source of AC power although, as generally pictured in this figure, the monitor 50 can certainly be configured to be either battery (to include capacitive storage) or AC powered, although a battery or other mobile power source is generally preferred in the case of a monitor that is attached to a wheelchair.

Figure 2:
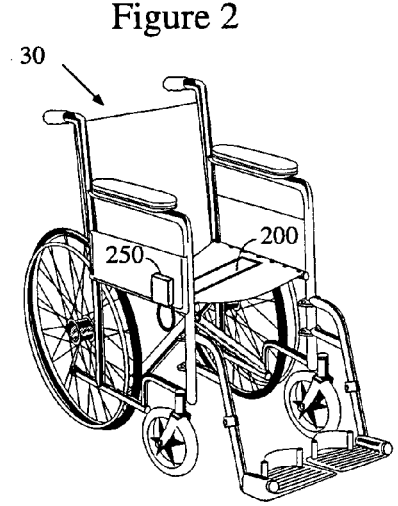
FIG. 2 contains an illustration of another preferred arrangement, wherein a monitor/mat combination is used to monitor a patient in a wheelchair.

In another common arrangement, and as is illustrated in FIG. 2, a pressure sensitive chair sensor 200 might be placed in the seat of a wheel chair or the like for purposes of monitoring a patient seated therein. As has been described previously, a typical configuration utilizes a pressure sensitive mat 200 which is connected to electronic chair monitor 250 that is attached to the chair 30. Because it is anticipated that the patient so monitored might want to be at least somewhat mobile, the monitor 250 will usually be battery powered and will often signal a chair-exit event via an integral speaker (or, e.g., via a wireless link), rather than via a hardwired nurse-call interface.

Broadly speaking, the electronic patient monitors that are referred to herein work by first sensing an initial status of a patient, and then generating a signal when that status changes (e.g., the patient changes position from laying or sitting to standing, the sensor changes from dry to wet, etc.).

General information relating to mat sensors and electronic monitors for use in patient monitoring may be found in U.S. Pat. Nos. 4,179,692, 4,295,133, 4,700,180, 5,600,108, 5,633,627, 5,640,145, 5,654,694, and 6,111,509 (which concerns electronic monitors generally), and U.S. Pat. No. 7,079,795 (which concerns using pulse width modulation to control an alarm volume). Additional information may be found in U.S. Pat. Nos. 4,484,043, 4,565,910, 5,554,835, 5,623,760, 6,417,777, 7,078,676 (sensor patents), U.S. Pat. No. 7,030,764 pertaining to monitor and method for reducing the risk of decubitus ulcers, and U.S. Pat. No. 5,065,727 (holsters for electronic monitors), the disclosures of all of which patents are all incorporated herein by reference. Further, U.S. Pat. No. 6,307,476 (discussing a sensing device which contains a validation circuit incorporated therein), and U.S. Pat. No. 6,544,200 (for automatically configured electronic monitor alarm parameters), U.S. Pat. Nos. 6,696,653 and 6,858,811 (for a binary switch and a method of its manufacture), U.S. Pat. No. 6,864,795 (for a lighted splash guard), U.S. Pat. No. 7,079,036 (for alarm volume control using pulse width modulation) and U.S. Pat. No. 6,897,781 (for an electronic patient monitor and white noise source for soothing a patient to sleep after they have turned) are similarly incorporated herein by reference.

Note that the instant invention is suitable for use with a wide variety of patient sensors in addition to pressure sensing switches including, without limitation, temperature sensors, patient activity sensors, cardiac sensors, toilet seat sensors (see, e.g., U.S. Pat. No. 5,945,914), wetness sensors (e.g., U.S. Pat. No. 6,292,102), bed pressure sore sensors (e.g., U.S. Pat. Nos. 6,646,556, 6,987,232, and 7,078,676), thermal sensors (U.S. patent application Ser. No. 11/132,772), etc. Thus, in the text that follows the terms "mat" or "patient sensor" should be interpreted in its broadest sense to apply to any sort of patient monitoring sensor or device, whether the sensor is pressure sensitive or not.

PREFERRED EMBODIMENTS

In accordance with a first preferred aspect of the instant invention, there is provided a patient monitor that is automatically disabled when a caregiver enters a room and then is automatically reactivated after the caregiver leaves and/or is manually reactivated by the caregiver while still in the room.

According to a first preferred embodiment, there is provided a patient monitor that will sense the presence of a transmitter that is carried by the caregiver and then that will automatically suspend its audible or other alarm during the time the caregiver is proximate to the patient. It will then automatically reactivate its alarm function and/or its monitoring function after the caregiver's transmitter can no longer be sensed, e.g., after the caregiver has moved away.

Figure 4:
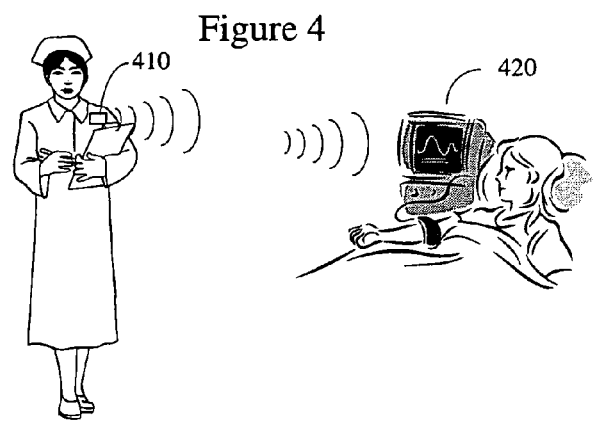
FIG. 4 illustrates in a general way how a preferred wireless embodiment of the instant invention would operate in practice.

Consider, for example, the embodiment of FIG. 4. In this preferred arrangement, the caregiver will carry, preferably in the form of a badge or pager, an electronic device 410 that transmits an inhibiting ultrasonic signal to a receiver that is located within each electronic patient monitor 420 in the room. Preferably, and as a power saving measure, the transmitter 410 will broadcast an ultrasonic pulse train (e.g., a pulse will be transmitted every second or, in some embodiments, at longer or shorter intervals as needed). Of course a continuous broadcast is certainly possible, but would likely drain the transmitter 410 battery at a higher rate than would be normally desired.

It should be noted that the use of an ultrasonic transmitter (e.g., via an ultrasonic transducer)/receiver combination is a preferred hardware configuration. In the preferred arrangement, the transducer will be operated at about 20 milli-watts of power at a frequency of about 40 kHz. However, that configuration is not required and those of ordinary skill will recognize that many alternative arrangements to an ultrasound-based transmission scheme are possible (e.g., IR). Further, there are many standard wireless communications protocols that could also be used to send a signal to the monitor including, without limitation, WiFi, RF, Bluetooth, 802.11 family, ZigBee, IRDA, etc. Of course, there are many conventional devices with the capability of sending an inhibiting signal including PDAs and cell phones (e.g., using Bluetooth), laptop computers (e.g., using WiFI, 802.11, Bluetooth, etc.). Thus, although the preferred embodiment would utilize custom electronics in the form of a badge, clearly more familiar hardware could be used instead.

Within each monitor 420 will preferably be an ultrasonic receiver (e.g., an ultrasonic transducer) that, upon receipt, recognition, and verification of the presence of the appropriate signal, will preferably suspend broadcast of its local audio alarm and, optionally, suspend transmission of the alarm to a remote site such as a nurses' station. Additionally, in the preferred embodiment one or more monitoring functions of the unit will continue to be suspended so long as the inhibiting signal is sensed. More specifically, in the preferred embodiment if the monitor 420 is currently issuing an audible alarm and the transmitter 410 is sensed, the audio alarm will be terminated. Whether or not visual alarms (e.g., blinking lights) that might be present on the monitor 420 will also be terminated is a design choice, but in the preferred embodiment the visual alarm indicators will continue after the caregiver enters the room, thereby making it possible for him or her to determine which monitor was originally sounding the alarm in, for example, a case where multiple monitor types are used, visual indicators could potentially designate the source of the alarm. Additionally, many patient alarms are configured to sound a local alarm and to also transmit an alarm signal (either wirelessly or via wiring) to a remote location such as a nurses' station. For example, many patient monitors utilize a facility's nurse call system to augment its local audio alarm by transmitting a signal to a remote nurses' station by, for example, closing or opening a relay, sending a message via a standard computer network, etc. Of course, those of ordinary skill in the art will recognize that the exact means by which the nurses' station is contacted will vary depending on the facility. The transmission of the alarm signal to the remote location may or may not be suspended upon the entry of the caregiver into the room according to the desires of the designer and/or caregiver. However, in the preferred embodiment the remote alarm will also be temporarily suspended, if for no other reason than to inform other staff members that the patient is being attended to. As a specific example, if the monitor 420 has closed a normally-open nurse call switch, such switch might be held opened until the caregiver leaves the vicinity of the patient, at which time the patient's condition will once again be checked and the nurse call triggered if necessary.

In another preferred embodiment, the monitor 420 will only cease broadcast of its alarm signal upon verification that an authorized transmitter is actually present in the room, thereby tending to decrease the probability that the alarm will be wrongly terminated by environmental or other random noise (e.g., jingling a set of keys can generate a sufficient ultrasonic signal to be recognized as such by many ultrasonic receivers). Preferably, the monitor 420 will only cease broadcasting its audio alarm if it receives and identifies, by way of example only, three or more consecutive pulses from transmitter 410. For example, if a first inhibiting pulse is believed to be identified, the preferred monitor 420 logic will then look for at least two subsequent pulses within narrow time windows following the initiating pulse. For example, if the inhibiting/identifying pulses are designed to be one second apart, then one and two seconds after the triggering pulse is detected two additional signal pulses would be expected. Preferably some small degree of variation in the timing would be allowed (e.g., plus or minus 0.1 seconds, or some percentage of the time interval between them, etc.). Of course, if one (or both) of the subsequent pulses is missing, the alarm will preferably not suspend its alarm function at that time. On the other hand, if the (for example) three pulses are all determined to be present the receiving monitor 420 will preferably suspend the sounding of its audio alarm. Those of ordinary skill in the art will recognize that this is just one of any number of different methods that could be used to validate the input signal and reduce the risk of unintended monitor alarm suppression.

After the patient monitor 420 senses and preferably confirms that the caregiver is proximate thereto, it will preferably suspend the sounding of its audio alarm, if such is currently being sounded. As has been mentioned previously, this may or may not be accompanied by cessation of any visual alarm cues (such as blinking lights) according to the preferences of the programmer or, if the software logic provides for it, the preferences of the caregiver.

Of course, in some cases the caregiver might enter the room at a time when no alarm is sounding. In that instance, the preferred option would be to have the alarm functions of the monitor(s) disabled or suspended until such time as the caregiver leaves, thereby allowing the caregiver to work with the patient (e.g., in the case of an exit monitor, to reposition the patient in the bed, to provide physical therapy, etc.) without triggering an alarm. Thus, if an alarm situation arises while the caregiver is in the room, in the preferred embodiment no audible alarm will be sounded, although a visual alarm and/or a remote alarm might still be utilized. Obviously, exactly how this particular aspect will be implemented is a design choice that is well within the abilities of one of ordinary skill in the art. In some circumstances, the opposite function might be provided, i.e., if a new patient condition that warrants an alarm arises while the caregiver is in the room, only such new alarms will be sounded. In other instances, only certain kinds of new alarm conditions will be suppressed, e.g., a cardiac alarm might sound audibly if a change in the patient's condition calls for it while the caregiver is present, whereas a bed or other exit alarm might not be sounded. Those of ordinary skill in the art will be able to readily devise many other sorts of operational logic.

After the caregiver has finished his or her business in the patient's room and moves to exit the room, the transmitter 410 will be taken away from the vicinity of the monitor 420 by such movement, thereby eventually removing it from the reception range. Note that, depending on the technology that is used, the reception range might extend to a few feet (e.g., if RF or ultrasonic are used), a line of slight (IR, etc.), etc. Of course, as an alternative the caregiver could remain in the room and manually deactivate the transmitter, thereby causing the monitor to respond as though the caregiver had left. This might be useful for any number of reasons, but one example of when this ability would be useful would be when a caregiver wishes to determine whether there are any alarm conditions in the room that must be attended to before actually leaving.

In any case, once the caregiver has left the vicinity of the patient the monitor 420 will preferably resume monitoring the patient and generating alarms according to its programming. Note that there are two preferred ways that this might happen. According to a first preferred variation, the monitor will resume monitoring immediately upon sensing the absence of the caregiver and, thus, any patient condition that merits it will result in an immediate audible alarm. One advantage of this approach is that if there is a new (or even a continuing) problem, the caregiver will likely hear the audio alarm before he or she is too far removed from the patient, thereby saving a return trip. In another preferred arrangement, the monitor 420 will become reactivated some period of time after the caregiver has departed (e.g., five seconds thereafter). Those of ordinary skill in the art will be able to determine the circumstances in which when each type of approach might be most beneficial and this might be different, depending on the type of monitor.

According to another preferred arrangement, there is provided a transmitter/monitor combination substantially as described above, but wherein instead of the monitor 420 automatically suspending its monitoring or alarm functions when the caregiver is in the vicinity thereof, instead such suspension only takes place after a specific act by the caregiver (e.g., by pressing a "hold" switch on the transmitter or placing a magnet on the monitor case). The monitoring function will then automatically resume, preferably after the caregiver has left the vicinity of the patient or after some predetermined period of elapsed time.

In one preferred embodiment, the caregiver's badge 410, pager, etc., will be equipped with an activation switch and, preferably, the device 410 will not begin to broadcast its suppressing pulse until after the switch is activated. By way of example, this would allow a caregiver to view the situation in the patient's room while the alarms were still sounding. This might be desirable in some instances, as it would allow the caregiver to quickly assess the situation before silencing the alarm(s). If the alarm condition is sufficiently serious, the caregiver can immediately help the patient, knowing that the still-sounding alarm will summon additional help. Of course, after the transmitter 410 has been activated, the patient monitors will preferably react in the same fashion as has been described previously. Similarly, and in another preferred embodiment, the badge 410 will be equipped with a deactivation switch or button (which might be the same physical button as was used to activate the transmitter) to allow the caregiver to manually terminate the broadcast of the inhibiting signal while still in the patient's room. The deactivation switch might initiate a separate reactivation signal, or simply terminate the broadcast of the inhibiting signal. Obviously, if the broadcast is terminated, the monitor will reactivate as though the caregiver had left reception range. One advantage of this feature is that it would allow the caregiver to see if there were any remaining alarm conditions that needed to be addressed before he or she leaves the room. If a separate reactivation signal is used, it could be designed to replace the inhibiting signal (e.g., the inhibiting signal will be turned off and the reactivation signal activated) or override the inhibiting signal (e.g., the inhibiting signal can remain on while the reactivation signal is broadcast) as the designer sees fit.

Figure 3:
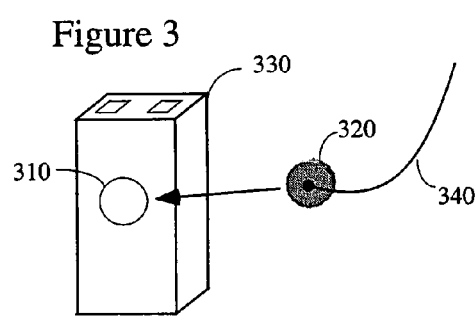
FIG. 3 a preferred embodiment of the instant invention which utilizes a magnet that is tethered to a caregiver so that when the caregiver moves away from the patient the tether pulls the magnet away from the monitor, thereby causing it to reactivate.

In another preferred embodiment, and as is generally indicated in FIG. 3, there is provided a patient monitor 330/activator 320 combination that is designed to disable a specific patient monitor 330 by bringing the activator into contact with or close proximity to the monitor 330. In the preferred arrangement, the activator 320 will be a magnet that is attached via a tether 340 to a caregiver's clothing, key chain, etc. Preferably, the magnetic inhibitor 320 will be placed in contact with a predefined region 310 on the face of the monitor 330 when the caregiver wishes to disable or suspend the monitor's operations. In one preferred embodiment, the monitor 330 will contain a Reed switch, Hall effect, or similar proximity sensor therein that allows it to sense the presence of the magnetic inhibitor 320. Then, during such time as the inhibitor 320 is positioned on the face of the monitor 330, the alarm functions will be disabled and/or the audible alarm will be silenced.

Preferably, the attachment region 310 will be designed so that a magnet will adhere thereto, thereby freeing the caregiver's hands to work with the patient. Of course, after the magnetic inhibitor 320 is removed from its face, the monitor 330 will preferably resume its normal operations, either immediately or after a predetermined time delay according to its programming. One advantage of this embodiment is that since the inhibitor 320 will preferably be tethered to the caregiver, he or she will not be able to leave the patient's side without reactivating the monitoring and alarming functions so long as the inhibitor 320 is so attached. This arrangement would be particularly useful when working with exit monitors and especially in those circumstances where the patient needs to be temporarily moved within the bed. Although most exit alarms have a "hold" or similar switch which allows a caregiver to manually suspend the operation of the unit for some period of time, it is far too easy to leave the patient's vicinity without reactivating the monitor, hence tethering the caregiver to the magnetic inhibitor 320 will tend to reduce the risk that this will happen. Further, since some patients are prone to disabling their own monitors (and thereafter, for example, leaving the bed undetected), in some variations the monitor logic might require that the magnetic inhibitor 320 be in place before any of the monitor's operational parameters can be modified (e.g., the module cannot be shut off, the exit delay extended, etc., without having the magnetic inhibitor 320 in place), thereby thwarting such a patient.

Figure 6:
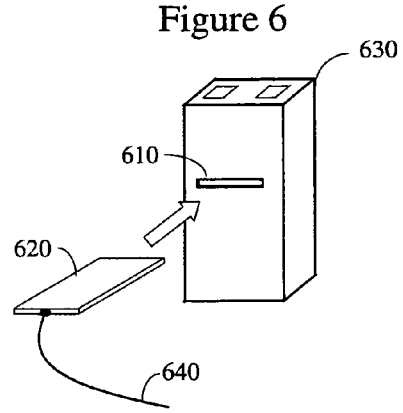
FIG. 6 illustrates a preferred embodiment, wherein a tethered key is inserted into a patient monitor, thereby suspending its monitoring and/or alarm functions and, optionally, allowing supervisor program to internal operating parameters.

Those of ordinary skill in the art will recognize that an audible or silent patient monitor alarm might be disabled according to the instant invention in many different ways. For example, consider the embodiment of FIG. 6, which is substantially similar to the embodiments discussed previously, but wherein a key 620 is used to deactivate or suspend the operations of the patient monitor 630. As an example of how this embodiment might work in practice, when the caregiver enters the room key 620 is inserted into the key slot 610, thereby silencing its alarm. In the preferred arrangement, the key 620 will be tethered to the caregiver via cord 640 so that when the caregiver leaves the side of the patient the key 620 will be withdrawn from the monitor 630, after which the monitor 630 will resume its normal operations. If, for example, the outer surface of the key slot 610 were made to be conductive, the monitor 630 would be able to sense its presence and absence from the slot 610 via a simple continuity check, thereby making it possible to deactivate and reactivate the monitor 630 on demand. On the other hand, if the outer surface of the key were made to be nonconductive, insertion of the key 620 could be used to "break" a circuit, thereby terminating power to the unit, creating a condition discoverable by a continuity check, etc. Those of ordinary skill in the art will be readily able to devise similar schemes for suspending the monitor's alarm operations.

In still another preferred arrangement, the key 620 will take the form of a thumb drive, removable non-volatile storage card (e.g., compact flash, secure digital, memory stick,) etc. In one preferred embodiment, the memory card will have a data such as a serial number written thereto that can be used by the monitor to determine whether or not to silence or disable its alarm. As has been discussed previously, orderlies might be given different serial numbers than nurses depending on the severity of the condition that initiated the alarm. In another preferred embodiment, various items of information will be written from the monitor back to the memory key while it is inserted (e.g., an insertion time stamp, response time to silence the alarm, the identification of the responding caregiver, or other performance or operational characteristics of the monitor, etc.).

According to another preferred embodiment and substantially as described above, there is provided a patient monitor that will be automatically disabled temporarily (and/or its monitor functions likewise suspended) while a caregiver is proximate to a patient and then will be automatically reactivate after a predetermined period of time. For example, upon sensing the presence of a caregiver proximate to a patient monitor, its alarm function might be suspended in, say, increments of five seconds, during which time the caregiver would presumably be able to attend to the alarm that brought him or her into the room. In another common scenario, automatic suspension of a patient exit alarm after a caregiver is sensed to be proximate to the patient would allow the patient to be temporarily moved from the bed (e.g., helped to the restroom) or relocated within it (e.g., turned, moved to a new location in the bed for purposes of decubitus ulcer prevention, etc.) without causing the exit alarm to be activated.

According to still another preferred aspect of the invention, there is provided a patient monitor substantially as described above that can be manually disabled while a caregiver is proximate to a patient and then automatically reactivates after the caregiver has left the patient's vicinity. This embodiment is similar to the embodiment discussed in connection with FIG. 4, except that the transmitter will preferably only broadcast its inhibiting signal after receipt of some manual instruction from the caregiver. For example, in the transmitter embodiment 410 a button or similar switch might be provided on the face of the unit 410 that could be used by a caregiver to initiate transmission of the inhibiting signal. So, when a nurse or other caregiver enters a room and is confronted with one or more audio alarms, activating the switch provided will preferably make it possible to simultaneously silence all of the alarms in the room. The transmitter 410 would then preferably continue to send its inhibiting signal for some period of time after activation or until the caregiver manually terminates the broadcast.

In one preferred embodiment, the transmitter 410 will broadcast its signal for a predetermined period of time after activation (e.g., for five minutes). In another preferred arrangement, the inhibiting signal will be transmitted until manually deactivated by the caregiver. Continuing with the discussion of the previous embodiment, in one variation the transmitter 410 will begin to emit a warning sound (such as a low "beep") after some period of time has passed to remind the caregiver that the inhibiting signal is being transmitted or as an indication of impending timer exhaustion, in which case the caregiver could extend the deactivation interval (e.g., by manual reactivation of a button on the face of the transmitter 410) or not depending on the amount of work remaining to be accomplished. Note that it is preferable that if the inhibiting signal is terminated the patient monitors will immediately reactivate. As has been mentioned previously, this would be especially useful in the instance where a caregiver is in the process of leaving the patient's room with a monitor-related issue unintentionally unresolved. Additionally, this feature would allow the caregiver to quickly summon more help into a room by reactivating the alarms, e.g., by manually terminating the broadcast of the inhibiting signal.

In one preferred embodiment the monitor's audio speaker will be used both for sounding the alarm and receipt of the inhibiting signal. That is, those of ordinary skill in the art will recognize that a speaker can be used as a microphone in some instances. In this embodiment, the speaker will be used as such, with the preferably ultrasonic inhibiting signal being sought during short pauses in the sounding of the alarm when the speaker is silent. Further, the speaker will preferably be a cone-type loudspeaker integral to the monitor but, clearly, it could be any sort of device that can emit sound, including power amplifier/speaker combinations of various sorts. Additionally, the speaker could be a piezoelectric or similar device and, especially preferably, it could be a piezoelectric device that is driven directly from a microprocessor without an intervening amplifier. Thus, for purposes of the instant disclosure, when the term "speaker" is used herein, that term should be broadly construed to include any sort of sound emitting device including, if necessary, a power amplifier or other support electronics.

Figure 5:
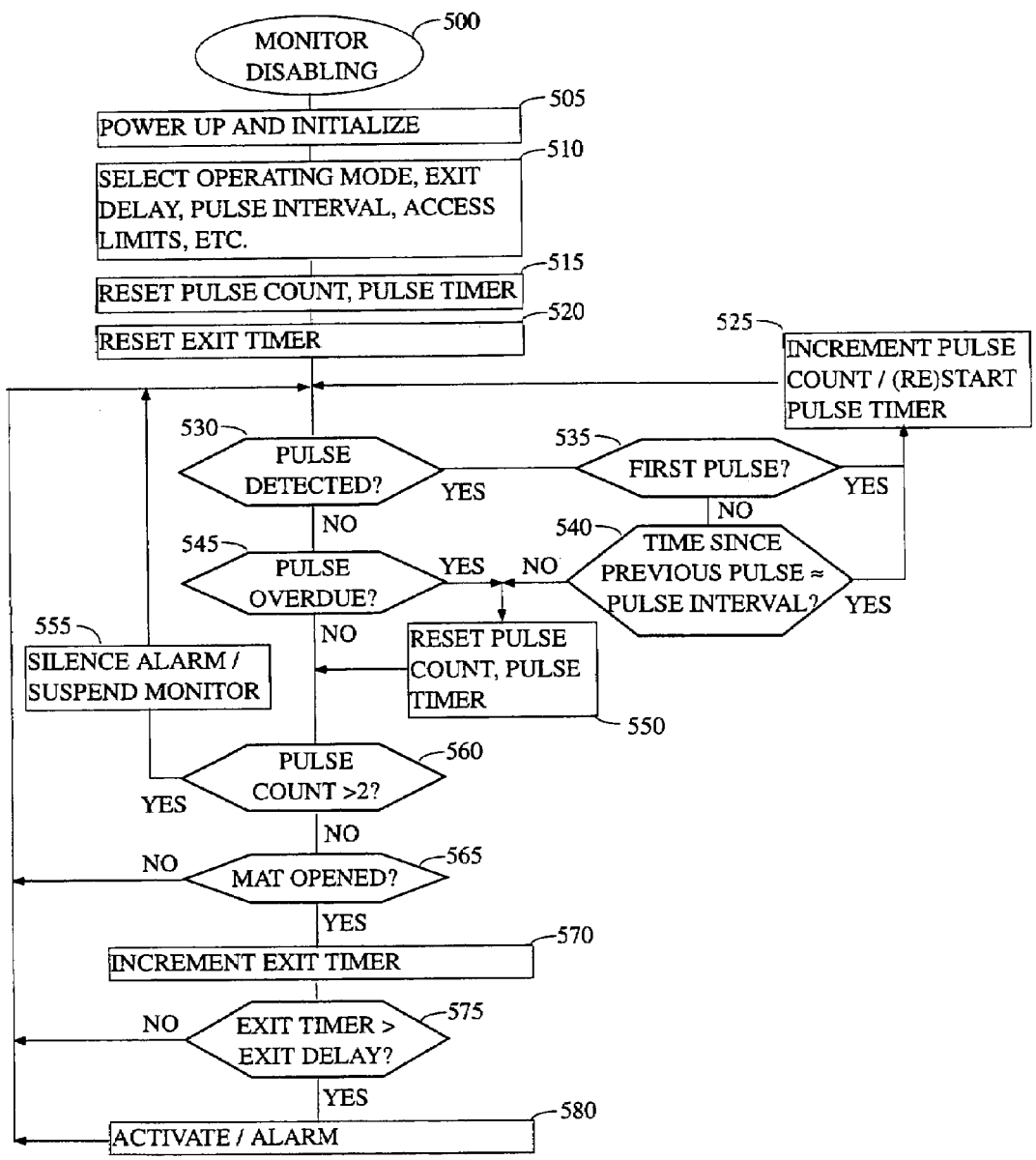
FIG. 5 contain a preferred logic that would be suitable for use with a patient monitor designed according to the instant invention.

FIG. 5 contains a preferred operating logic 500 for use with one aspect of the instant invention. This figure contains a logic flowchart that would be suitable for use within a patient monitor that operates according to one preferred embodiment. As is indicated, as a preferred first step 505 the patient monitor will, upon power up and/or reset, initialize various of its internal program variables according to methods well known to those of ordinary skill in the art.

Next, the instant invention will preferably determine various operational parameters such as its operating mode, an exit delay (i.e., in the event that the monitor is designed to sound an alarm on a patient exit), an inhibiting signal pulse interval (step 510), etc. The operating mode parameter will preferably control whether the alarm function will be suspended automatically or manually upon the entry of the caregiver into the room (e.g., the monitor itself might have a switch that suspends the monitor operation and only then only resumes alarming again after the caregiver has left the room). The operating mode parameters may or may not be made to be modifiable by the caregiver/user and, in some cases as discussed hereinafter, the users who are allowed to modify operating parameters may be limited based on their authority, experience level, etc. For a more general discussion, see the text below that deals with MSAA signals. The exit delay parameter is only one of many possible alarm specific parameters that might be given a default value at this step. For purposes of specificity in the discussion that follows, the patient monitor will be assumed to be an exit monitor. However, those of ordinary skill in the art will understand how the following discussion can be applied to other sorts of patient monitors in other circumstances.

As a next preferred step, the pulse count and pulse timer variables will be reset, e.g., set to be equal to zero (step 515). In the preferred embodiment and as is described in greater length hereinafter, various characteristics of the inhibiting signal train (e.g., the pulse interval, pulse duration, pulsed data translation, pulse count, etc.) will be used to verify whether or not an inhibiting signal has been detected. For purposes of this example, the pulse interval is defined to be the time interval between the successive inhibiting signal pulses that are transmitted by the caregiver's transmitter, assuming for purposes of illustration only, that the caregiver's transmitter utilizes a pulsed signal.

Finally, and as a last preferred preparatory step, the exit timer will be reset to zero (step 520). Note once again that it has been assumed for purposes of illustration only that the patient monitor is an exit-type monitor. Those of ordinary skill in the art will recognize that it is customary to allow the caregiver to specify a parameter that controls the amount of delay after a patient's absence is noted before the alarm is sounded. In most cases, this parameter will vary from zero (i.e., no delay) to a few seconds. Clearly, any number of other performance or alarm related parameters might be specified by the user and/or set by default at this step, depending on what type of monitor and user parameters are selected.

Next, the instant method preferably enters a main event loop (steps 525-580, inclusive). As a first step, the instant patient monitor will preferably check to see if an inhibiting signal pulse is present (step 530). Obviously if a pulsed signal is not used, the instant invention will alternatively check for the presence of the caregiver's signal, whatever its form or format. Those of ordinary skill in the art will understand how the instant operating logic would need to be changed in the event that the caregiver's signal is not a periodic pulse (e.g., a pulsed data signal).

If an initiating pulse is detected (the "YES" branch of decision item 530) and if it is the first pulse (the "YES" branch of decision item 535), the pulse count will preferably be incremented (i.e., set to unity) and the pulse timer will be started (step 525). In the preferred embodiment, the pulse timer will be used to determine the time at which the next pulse is expected based on the predetermined pulse interval. Note that this function might involve the use of a clock chip, a software timing loop, or any number of other variations.

On the other hand, if the signal pulse that is detected is not the first pulse (the "NO" branch in decision item 535) and if the time since the previous pulse exceeds the pulse interval, the validation process will preferably be restarted (the "YES" branch of decision item 545). If a pulse is not overdue the logic preferably continues by checking the pulse count (decision item 560). If the pulse count is less than or equal to 2, the preferred logic continues to check the condition of the mat (decision item 565) or other patient sensor. On the other hand, if the pulse count is greater than 2 (the "YES" branch of decision item 560), preferably any currently sounding alarms will be silenced and the monitor operations will be suspended (step 555).

If the mat is not opened (the "NO" branch of decision item 565), the instant invention preferably branches to the top of the event loop. Of course, those of ordinary skill in the art will recognize that the "mat opened?" test could readily be modified to check the status of any sort of patient sensor.

Next, and if the pressure has been released from the mat (the "YES" branch of decision box 565), preferably the exit timer will be incremented (step 570), the intent being to delay sounding an alarm until the exit delay interval has been exceeded (decision item 575). Of course, once that happens, an audible alarm will preferably be activated (step 580) to notify the caregiver of the patient's absence from the bed or other support surface.

Note that if the caregiver is found to be proximate to the monitor (the "YES" branch of decision item 560), the patient's condition is preferably never checked (decision item 565), although that it not a requirement and different programmers may handle this aspect of the invention differently. Upon the caregiver leaving the vicinity of the patient, the patient monitor's alarm function will be activated (see, especially decision item 545 and step 580).

As has been explained previously, steps 530-550 are broadly concerned with detection and verification of a caregiver's inhibiting signal. In the example of FIG. 5, this signal is a series of equally spaced ultrasonic pulses and, thus, the presence and timing (including determination of the intervals between successive pulses) of such pulses is used for purposes of verification and to reduce the likelihood that a noise burst will inadvertently silence a monitor. Although it is certainly possible that an isolated noise event might "fool" the monitor once, it is unlikely that multiple pulses will be observed at the proper time spacing by chance.

According to still another preferred embodiment, there is provided a system and method for temporarily suspending the operation or alarm of a patient monitor which is substantially as described above, but wherein a plurality of different signals are potentially receivable by the monitor. In this arrangement, different caregiver transmitters might generate different inhibiting signals (e.g., pulses that are transmitted at different frequencies or different time intervals, etc., could be used to differentiate between caregivers, as could different signal source types e.g., IR versus RF, etc.). In turn, the monitors would then be programmed to suspend their alarms (or not) depending upon which of the different transmitted signals is detected. For example, cardiac monitors might be programmed to suspend operation upon receipt of one signal and exit monitors upon receipt of another. In this instance, transmitters that control the silencing of the critical cardiac monitor would generally only be given to nurses or other caregivers with cardiac training. Thus, an orderly or nurses aid—who might be fully qualified to respond to an exit event, a turn need, or a wetness alarm but is not qualified to handle a cardiac emergency—would be given a badge which does not automatically silence the cardiac monitor upon entry into the room. In other embodiments, the amount of time that the monitor(s) will be deactivated might be made to depend on which caregiver is present. In one arrangement and for certain type of monitors, a less experienced caregiver will be given a shorter period of time than an experienced one, thereby causing an alarm to be sounded (and help to be summoned) if the inexperienced staff person is unable to resolve the problem quickly. In other embodiments, the inexperienced caregiver's signal will silence the monitors for a longer period of time than the signal that is associated with an experienced one, thereby allowing the novice caregiver more time to complete the appointed task. For purposes of clarity in the text that follows, where multiple inhibiting signals are used and where different signals are accorded different functionality or privileges by the patient monitor programming, such signals will be referred to as monitor specific access authority ("MSAA") signals.

In another preferred arrangement, there is provided an apparatus for temporarily suspending the operation or alarm of a patient monitor wherein a transmitted signal is provided that will automatically reactivate the alarms that were previously silenced while the caregiver entered the room. This function could prove to be useful where a caregiver enters the room and automatically deactivates the various alarms, but thereafter determines that additional assistance may be needed from another staff member. In such an instance, preferably the transmitter will be provided with a signal (or a lack of an inhibiting signal) that notifies the monitors to resume sounding their respective alarms. Note that in this context the term "signal" is used in the broadest possible sense to include instances where the transmitter emits a distinctive signal (e.g., one that is longer in duration, different in frequency, is modulated, is coded uniquely, etc., from the suppressing signal) at the request of the caregiver or one that ceases to transmit its customary inhibiting signal, thereby causing the monitor to react as though the caregiver has left the vicinity of the patient and that its audible (and/or remote) alarms should be reactivated.

In still another preferred arrangement, the monitor(s) in a patient's room will be placed on hold and/or silenced when the door to the room is opened. Obviously, this approach would not be effective for some facilities, but in others (e.g., where the patients are suffering from dementia, are in assisted living centers, are criminals, etc.) this could be a preferred approach. In some preferred embodiments, opening the door will trigger a proximity-type switch (e.g., a magnet) that causes a suppressing signal to be transmitted, which will be received and verified according to methods similar to those described above. An advantage of this sort of approach is that it would quiet in-room alarms when the caregiver enters the room, which may have a tendency to calm certain kinds of patients (e.g., patients for whom the alarms are troubling, patients who believe that the alarm will be ignored, etc.) thereby making it easier to work with them.

In a further arrangement, there is provided a system for automatically suspending the operation of a patient monitor, wherein is preferably provided a passive RFID-enabled (or similar technology) badge that is worn by the caregiver. In the preferred arrangement, RFID readers will be placed, for example, in patient room doorways within the institution. Then, each time a caregiver enters or exits a room that fact will be noted, and the patient monitors therein will respond accordingly. Further, and as has been discussed previously, preferably each caregiver's badge will be assigned a serial number which is readable by the RFID system. This configuration makes it possible to silence different ones of the patient's alarms based on the capabilities of the individual caregiver. Still further, in such an arrangement it would easily be possible to use the patient monitor of the instant invention to track the comings and goings of each caregiver by noting the times that each RFID is sensed. As an extension of this idea, it would also be possible to determine the response time of the staff to an alarm condition, the individual who responded to the alarm condition, etc., using RFID or similar technology, wherein each caregiver can be provided with a unique or otherwise distinguishable inhibiting signal, i.e., a MSAA signal.

Finally, in still another preferred variation, there is provided a system for automatically suspending the alarm of a patient monitor in the presence of an inhibiting signal, wherein the monitor is provided with one or more modifiable operating parameters that can be modified by the caregiver. Further, and most preferably, these parameters will be made to be adjustable or not depending on which sort of inhibiting signal is present. That is, in one preferred arrangement only caregivers of certain levels of experience (as measured by the badges/transmitters they are given) will be allow to modify the operating parameters. Such caregivers would be made identifiable by the monitor by issuing them transmitters that broadcast a predetermined inhibiting signal. That is, in a preferred embodiment a plurality of inhibiting signals will be provided, some of which will be uniquely associated with higher level (or more responsible) caregivers. The monitor will then be able to readily determine which caregivers are authorized to modify its parameters.

As a simple example of this scenario, consider an exit alarm which utilizes, among others, a delay parameter that controls the length of time between when the sensor detects the patient's absence and when the alarm begins to sound. In this variation of the instant invention, it might be that if an orderly's badge/transmitter is identified, the alarm would be silenced, but the orderly would not be allowed to adjust the exit delay (or, potentially, any other operating parameter). On the other hand, and continuing with the instant example, if a nurse or other authorized caregiver is identified as being in the room and proximate to the patient monitor, such parameters could be made to be modified for only so long as an authorized inhibiting signal is sensed. This is another instance where the use of an MSAA signal would be beneficial. Those of ordinary skill in the art will readily be able to devise alternative variations of this embodiment.

CONCLUSIONS

A principal goal of the instant invention is to help prevent instances where a caregiver disables—either deliberately or accidentally—a patient monitor while working with a patient and then neglects to enable it again before leaving the room, thereby leaving the patient at risk of injury or death. Another broad goal of the instant invention is to automatically cease the sounding of audible alarms before the caregiver has even reached the patient's side, thereby speeding needed intervention. Another feature of the instant invention is its ability to disable some alarms in a room but not others, preferably according to the abilities or experience level (e.g., MSAA level) of the caregiver. This technology will tend to reduce instances where the caregiver is distracted by the alarms upon arrival and spends precious time silencing said alarms, time that could be used instead to treat the problem that necessitated the visit.

Note that if a microprocessor is utilized as a component of any device discussed herein, the only requirement that such a component must satisfy is that it must minimally be an active device, i.e., one that is programmable in some sense, that it is capable of recognizing signals from a bed mat or similar patient sensing device, and that it is capable of initiating the sounding of one or more alarm sounds in response thereto. Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e., erasable PLD's), SPLD's (i.e., simple PLD's), PAL's (programmable array logic), FPLA's (i.e., field programmable logic array), FPLS (i.e., fuse programmable logic sequencers), GAL (i.e., generic array logic), PLA (i.e., programmable logic array), FPAA (i.e., field programmable analog array), PsoC (i.e., programmable system-on-chip), SoC (i.e., system-on-chip), CsoC (i.e., configurable system-on-chip), ASIC (i.e., application specific integrated chip), etc., as those acronyms and their associated devices are known and used in the art. Further, those of ordinary skill in the art will recognize that many of these sorts of devices contain microprocessors integral thereto. Additionally, those of ordinary skill in the art will recognize that discrete electronic components could be assembled to create a circuit that exhibits at least a portion of the operating function of the instant invention. Thus, for purposes of the instant disclosure the terms "processor," "microprocessor" and "CPU" (i.e., central processing unit) should be interpreted to take the broadest possible meaning herein, and such meaning is intended to include any PLD or other programmable device (to include custom circuitry formed from digital and/or analog components) of the general sort described above.

Additionally, in those embodiments taught herein that utilize a clock or timer or similar timing circuitry, those of ordinary skill in the art will understand that such functionality might be provided through the use of a separate clock circuit or implemented in software within the microprocessor. It might further be obtained with discrete, linear, timers and logic circuitry: a microprocessor is not strictly required, but is merely convenient. Thus, when "clock" or "time circuit" is used herein, it should be used in its broadest sense to include both software and hardware timer implementations.

Note further that a preferred electronic monitor of the instant invention utilizes a microprocessor with programming instructions accessible thereby, where such programming instructions define the monitor's response to the patient. Although ROM is the preferred apparatus for storing such instructions, static or dynamic RAM, flash RAM, EPROM, PROM, EEPROM, or any similar volatile or nonvolatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, flash RAM card, a ROM card, a DVD disk, or loaded into the monitor over a wired or wireless network as needed. Additionally, those of ordinary skill in the art will recognize that the memory might be either internal to the microprocessor, or external to it, or some combination of the foregoing. Thus, "program memory" as that term is used herein should be interpreted in its broadest sense to include the variations listed above, as well as other variations that are well known to those of ordinary skill in the art.

Additionally, it should be understood that when the terms "alarm" and "indicating alarm" are used herein, those terms should be broadly interpreted to include traditional speaker-based audio alarms of the sort that are typically found inside of many patient monitors, as well as audible alarms that are broadcast at remote sites (e.g., in the hall outside the patient's room, at a nurses' station, etc.), as well as inaudible alarms such as blinking lights, electronic transmissions to pagers, calls to cell phones, etc. Further, in the event that the alarm is audible, the speaker will preferably be a cone-type loudspeaker or a piezoelectric device but, more generally and as has been discussed previously, could be any sound-emitting device. Still further, the alarm condition that merited that an alarm be sounded will typically be based directly on the patient's condition but, in some instances, it might be more in the form of a reminder. For example, an "alarm" might be generated at a predetermined time interval (e.g., at two hour intervals) to remind the staff to turn a patient to reduce the risk of decubitus ulcers. This reminder is, of course, at least indirectly related to the patient's condition and for purposes of the instant disclosure it will be considered to be an "alarm" as well.

Finally, it should be noted that the term "nurse call" as that term has been used herein should be interpreted to mean, not only various traditional wire-based (e.g., hard wired RS232, Ethernet, etc.) nurse call units, but also any system for notifying a remote caregiver of the state of a patient, whether that system is wire-based or a wireless (e.g., R.F., ultrasonic, IR link, etc.) system. Additionally, it should be clear to those of ordinary skill in the art that it may or may not be a "nurse" that monitors a patient remotely and, as such, the term "nurse" should be broadly interpreted to include any sort of caregiver, including, for example, untrained family members and friends that might be signaled by such a system.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A method of temporarily disabling an alarm function of a patient monitor, said patient monitor being at least for monitoring a changeable status of the patient, said alarm function being at least for initiating an alarm in response to a change in the changeable status of the patient, comprising the steps of:
    a. broadcasting from a mobile signaling device an inhibiting signal;
    b. moving said mobile signaling device proximate to said patient monitor;
    c. detecting within said patient monitor said inhibiting signal when the signaling device is proximate thereto;
    d. suspending said patient monitor alarm function upon detection of said inhibiting signal from said mobile signaling device; and,
    e. while said mobile signaling device is proximate to said patient monitor, manually initiating a reactivation signal from said mobile signaling device; and,
    f. receiving within said monitor said reactivation signal, thereby reactivating said patient monitor alarm function.

2. A method of temporarily disabling an audible alarm function of a patient monitor according to claim 1, wherein step (c) comprising the step of:
    (c1) detecting within said patient monitor said inhibiting signal when the signaling device is in a same room as said patient monitor.

3. A method of temporarily disabling an alarm function of a patient monitor according to claim 1, wherein said mobile signaling device broadcasts said inhibiting signal according to a protocol selected from a group consisting of WiFi, RF, Bluetooth, 802.11 family, ZigBee, IR, and ultrasonic.

4. A method of temporarily disabling an alarm function of a patient monitor according to claim 1, wherein step (a) comprises the step of:
    (a1) broadcasting from said mobile signaling device said inhibiting signal in response to manual activation of same by the caregiver.

5. A method of temporarily disabling an alarm function of a patient monitor according to claim 1, wherein said reactivation signal comprises cessation of said inhibiting signal.

6. A method of temporarily disabling an alarm function of a patient monitor according to claim 1, wherein said step (e) comprises the steps of:
    (e1) ceasing to broadcast from said mobile signaling device said inhibiting signal,
    (e2) broadcasting from said mobile signaling device a reactivation signal, and,
    (e3) reactivating said patient monitor alarm function upon detection of said reactivation signal in said patient monitor.

* * * * *